US012661081B2

(12) United States Patent
Ikeda

(10) Patent No.: US 12,661,081 B2
(45) Date of Patent: Jun. 23, 2026

(54) CONTROL DEVICE, CONTROL METHOD, AND CONTROL PROGRAM

(71) Applicant: FUJIFILM CORPORATION, Tokyo (JP)

(72) Inventor: Yuji Ikeda, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 212 days.

(21) Appl. No.: 18/632,295

(22) Filed: Apr. 11, 2024

(65) Prior Publication Data

US 2024/0268780 A1    Aug. 15, 2024

Related U.S. Application Data

(63) Continuation of application No. PCT/JP2022/038616, filed on Oct. 17, 2022.

(30) Foreign Application Priority Data

Oct. 21, 2021    (JP) ................................. 2021-172384

(51) Int. Cl.
*A61B 6/00*        (2024.01)
*A61B 6/46*        (2024.01)
(52) U.S. Cl.
CPC .............. *A61B 6/542* (2013.01); *A61B 6/461* (2013.01)
(58) Field of Classification Search
CPC ......... A61B 6/469; A61B 6/4441; A61B 6/06; A61B 6/545; A61B 6/587; A61B 6/582;
(Continued)

(56) References Cited

U.S. PATENT DOCUMENTS 6,370,218 B1 *    4/2002    Toth ..................... A61B 6/4085
                                              378/207
2002/0122534 A1 *  9/2002    Polkus ................... A61B 6/587
                                              378/205
(Continued)

FOREIGN PATENT DOCUMENTS

JP        2005-351736 A      12/2005
JP        2009-273603 A      11/2009
(Continued)

OTHER PUBLICATIONS

International Search Report issued in International Application No. PCT/JP2022/038616 on Dec. 27, 2022.
(Continued)

*Primary Examiner* — Irakli Kiknadze
(74) *Attorney, Agent, or Firm* — SOLARIS Intellectual Property Group, PLLC

(57)        ABSTRACT

A control device that controls an irradiation field of radiation with which a radiation detector is irradiated sets a first control amount that is an amount with which the irradiation field in a case where a required irradiation region which is an irradiation region of the radiation required in capturing a radiation image is a maximum region detectable by the radiation detector is extended outside the required irradiation region, to be smaller than a second control amount that is an amount with which the irradiation field in a case where the required irradiation region is inside the maximum region is extended outside the required irradiation region.

10 Claims, 13 Drawing Sheets

(58) Field of Classification Search
CPC ......... A61B 6/461; A61B 6/542; A61B 6/487;
A61B 6/12; A61B 6/488; A61B 6/52;
A61B 6/54; A61B 6/10; A61B 6/504;
A61B 6/58; A61B 6/5205; A61B 6/107;
A61B 6/08; A61B 6/42; A61B 6/5258;
A61B 6/547; A61B 6/40; A61B 6/544;
A61B 6/4233; A61B 6/548; A61B 6/00;
A61B 6/405; A61B 6/482; A61B 6/5217;
A61B 6/502; A61B 6/025; A61B 6/4035;
A61B 6/4208; A61B 6/4241; A61B
6/4266; A61B 6/4283; A61B 6/4291;
A61B 6/56; A61B 2560/0276; A61B
6/585; A61B 6/44; A61B 6/4411; A61B
6/566; A61B 6/464; H05G 1/00; H05G
1/64; G01N 23/04; G16H 50/30; G21K
5/10; G01T 1/17; G01T 1/40; H04N
23/71; G01V 5/22
USPC ........................................................ 378/145
See application file for complete search history.

(56) References Cited

U.S. PATENT DOCUMENTS

| | | | | |
|---|---|---|---|---|
| 2016/0270745 A1* | 9/2016 | Heath | .................. | A61B 6/4007 |
| 2019/0231283 A1 | 8/2019 | Jans et al. | | |
| 2020/0359977 A1 | 11/2020 | Ogawa et al. | | |

FOREIGN PATENT DOCUMENTS

| | | | |
|---|---|---|---|
| JP | 2013-094501 A | 5/2013 |
| JP | 2019-532718 A | 11/2019 |
| JP | 2020-185145 A | 11/2020 |

OTHER PUBLICATIONS

Written Opinion of the ISA issued in International Application No. PCT/JP2022/038616 on Dec. 27, 2022.
Extended European Search Report dated Dec. 12, 2024, issued in corresponding EP Patent Application No. 22883534.4.

* cited by examiner

Figure 15:
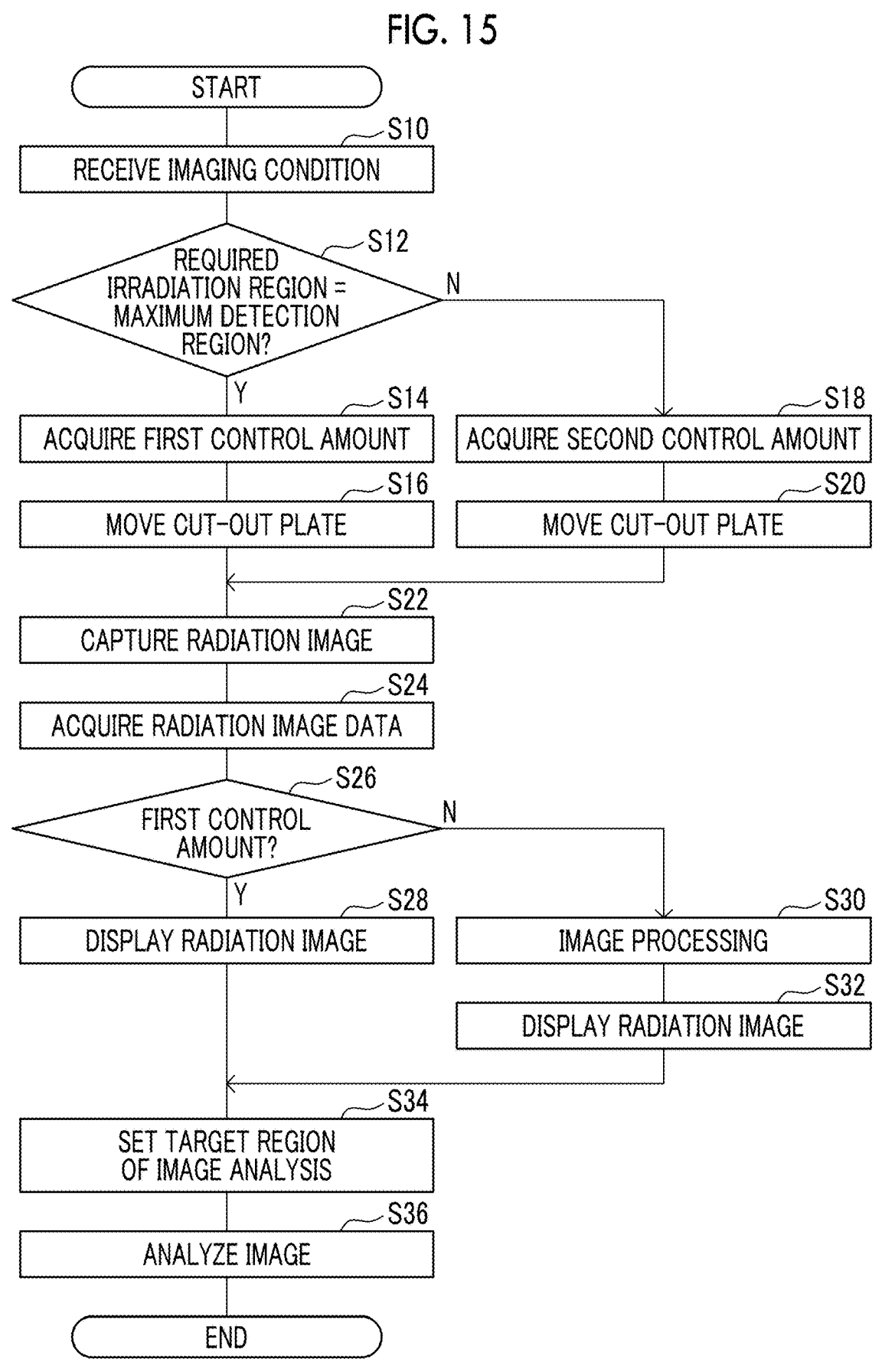

```
                    ┌──────────────┐
                    │    START     │
                    └──────┬───────┘
                           │         S10
                    ┌──────┴───────────────┐
                    │ RECEIVE IMAGING       │
                    │ CONDITION             │
                    └──────┬────────────────┘
                           │         S12
                     ╱─────┴──────╲
                    ╱  REQUIRED    ╲         N
                   ╱ IRRADIATION    ╲──────────────────┐
                   ╲ REGION =       ╱                   │
                    ╲MAXIMUM DETECT.╱                    │
                     ╲  REGION?    ╱                     │
                       ╲────┬─────╱                      │
                         Y  │                            │
                            │         S14                │         S18
                    ┌───────┴──────────┐      ┌──────────┴──────────────┐
                    │ ACQUIRE FIRST    │      │ ACQUIRE SECOND          │
                    │ CONTROL AMOUNT   │      │ CONTROL AMOUNT          │
                    └───────┬──────────┘      └──────────┬──────────────┘
                            │         S16                │         S20
                    ┌───────┴──────────┐      ┌──────────┴──────────────┐
                    │ MOVE CUT-OUT     │      │ MOVE CUT-OUT PLATE      │
                    │ PLATE            │      │                         │
                    └───────┬──────────┘      └──────────┬──────────────┘
                            │◄───────────────────────────┘
                            │         S22
                    ┌───────┴──────────┐
                    │ CAPTURE RADIATION│
                    │ IMAGE            │
                    └───────┬──────────┘
                            │         S24
                    ┌───────┴──────────┐
                    │ ACQUIRE RADIATION│
                    │ IMAGE DATA       │
                    └───────┬──────────┘
                            │         S26
                     ╱──────┴───────╲         N
                    ╱ FIRST CONTROL  ╲──────────────────┐
                    ╲ AMOUNT?        ╱                   │
                     ╲──────┬───────╱                    │
                        Y   │                            │
                            │         S28                │         S30
                    ┌───────┴──────────┐      ┌──────────┴──────────────┐
                    │ DISPLAY RADIATION│      │ IMAGE PROCESSING        │
                    │ IMAGE            │      │                         │
                    └───────┬──────────┘      └──────────┬──────────────┘
                            │                            │         S32
                            │                 ┌──────────┴──────────────┐
                            │                 │ DISPLAY RADIATION IMAGE │
                            │                 └──────────┬──────────────┘
                            │◄───────────────────────────┘
                            │         S34
                    ┌───────┴──────────┐
                    │ SET TARGET REGION│
                    │ OF IMAGE ANALYSIS│
                    └───────┬──────────┘
                            │         S36
                    ┌───────┴──────────┐
                    │ ANALYZE IMAGE    │
                    └───────┬──────────┘
                    ┌───────┴──────────┐
                    │      END         │
                    └──────────────────┘
```

CONTROL DEVICE, CONTROL METHOD, AND CONTROL PROGRAM

CROSS-REFERENCE TO RELATED APPLICATIONS

This application is a continuation of International Application No. PCT/JP2022/038616, filed on Oct. 17, 2022, which claims priority from Japanese Patent Application No. 2021-172384, filed on Oct. 21, 2021. The entire disclosure of each of the above applications is incorporated herein by reference.

BACKGROUND

1. Technical Field

The present disclosure relates to a control device, a control method, and a control program.

2. Description of the Related Art

JP2020-185145A discloses a technology for controlling a collimator to extend an irradiation region of an X-ray after highlighted display of a region of interest is finished in a region-of-interest highlight mode in X-ray image capturing.

JP2013-094501A discloses a technology for performing static image capturing by controlling a collimator to set an irradiation field of radiation as a region of interest in video capturing and, after the video capturing is finished, controlling the collimator to include the entire moving path of the region of interest in the irradiation field of the radiation in radiation image capturing.

SUMMARY

In the case of capturing the radiation image by performing irradiation with the radiation, blurriness may occur in an outer edge portion of the radiation image. In this case, the blurred portion that has occurred also reaches a subject portion in the radiation image, and image quality of the subject portion in the radiation image may be decreased.

The present disclosure is conceived in view of the above circumstances, and an object of the present disclosure is to provide a control device, a control method, and a control program that can suppress a decrease in image quality of a subject portion in a radiation image.

A control device according to an aspect of the present disclosure is a control device comprising at least one processor, the control device controlling an irradiation field of radiation with which a radiation detector is irradiated, in which the processor is configured to set a first control amount that is an amount with which the irradiation field in a case where a required irradiation region which is an irradiation region of the radiation required in capturing a radiation image is a maximum region detectable by the radiation detector is extended outside the required irradiation region, to be smaller than a second control amount that is an amount with which the irradiation field in a case where the required irradiation region is inside the maximum region is extended outside the required irradiation region.

In the control device according to the aspect of the present disclosure, the processor may be configured to set the first control amount and the second control amount to the same amount in a case where a difference between the maximum region and the required irradiation region is less than an amount by which the irradiation field is extended outside the required irradiation region using the first control amount.

In addition, in the control device according to the aspect of the present disclosure, an area of the irradiation field extended in accordance with the second control amount may be less than or equal to an area of the irradiation field extended using the first control amount.

In addition, in the control device according to the aspect of the present disclosure, a detection surface of the radiation detector for the radiation may have a rectangular shape, and the first control amount and the second control amount may be set in accordance with each side of the detection surface.

In addition, in the control device according to the aspect of the present disclosure, the processor may be configured to set a target region of image analysis in controlling a dose of the radiation to be inside a radiation image obtained in accordance with the first control amount or the second control amount by a predetermined amount.

In addition, in the control device according to the aspect of the present disclosure, the radiation image may have a rectangular shape, and the predetermined amount may be set in accordance with each side of the radiation image.

In addition, in the control device according to the aspect of the present disclosure, the processor may be configured to set the predetermined amount of the radiation image obtained in accordance with the first control amount to be smaller than the predetermined amount of the radiation image obtained in accordance with the second control amount.

In addition, in the control device according to the aspect of the present disclosure, the processor may be configured to, in a case where the required irradiation region is inside the maximum region, perform image processing of filling a portion outside the required irradiation region in a radiation image obtained in accordance with the second control amount with a color set in advance, and perform a control of displaying the radiation image after passing through the image processing on a display.

In addition, a control method according to another aspect of the present disclosure is a control method executed by a processor of a control device including at least one processor and controlling an irradiation field of radiation with which a radiation detector is irradiated, the control method comprising setting a first control amount that is an amount with which the irradiation field in a case where a required irradiation region which is an irradiation region of the radiation required in capturing a radiation image is a maximum region detectable by the radiation detector is extended outside the required irradiation region, to be smaller than a second control amount that is an amount with which the irradiation field in a case where the required irradiation region is inside the maximum region is extended outside the required irradiation region.

In addition, a control program according to still another aspect of the present disclosure is a control program for causing a processor of a control device including at least one processor and controlling an irradiation field of radiation with which a radiation detector is irradiated, to execute setting a first control amount that is an amount with which the irradiation field in a case where a required irradiation region which is an irradiation region of the radiation required in capturing a radiation image is a maximum region detectable by the radiation detector is extended outside the required irradiation region, to be smaller than a second control amount that is an amount with which the irradiation field in a case where the required irradiation region is inside the maximum region is extended outside the required irradiation region.

According to the present disclosure, a decrease in image quality of a subject portion in a radiation image can be suppressed.

BRIEF DESCRIPTION OF THE DRAWINGS

FIG. 15 is a flowchart illustrating an example of radiation image capturing processing.

DETAILED DESCRIPTION

Hereinafter, an embodiment of the disclosed technology will be described in detail with reference to the drawings.

Figure 1:
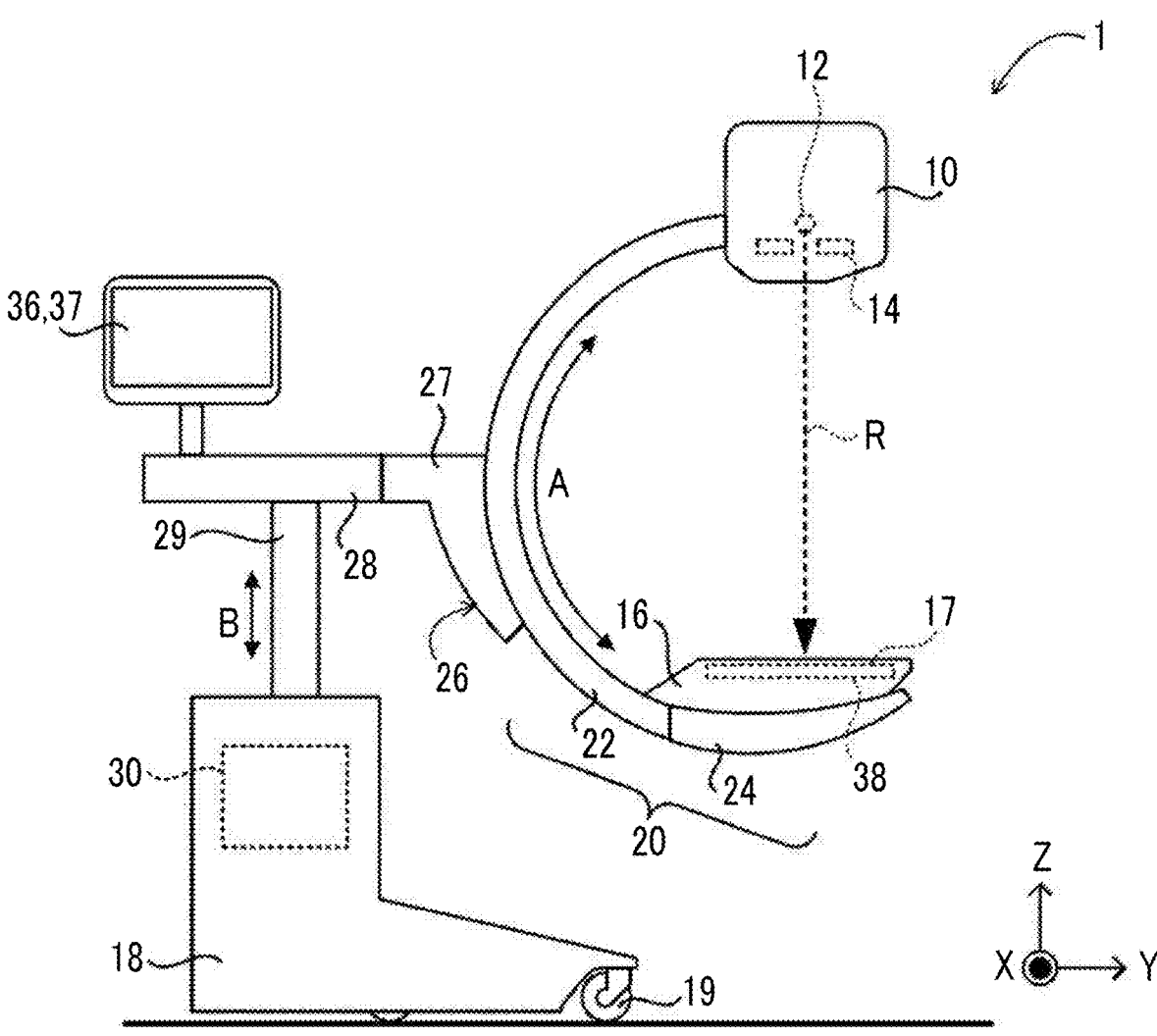
FIG. 1 is a side view illustrating an example of a configuration of a radiography apparatus.

First, a configuration of a mobile type radiography apparatus 1 according to the present embodiment will be described with reference to FIG. 1. As illustrated in FIG. 1, the radiography apparatus 1 comprises a C arm 20 including an arm part 22 and a holding part 24. A radiation emitting unit 10 that emits radiation R generated by a radiation source 12 is provided at one end of the arm part 22.

The radiation emitting unit 10 accommodates the radiation source 12 and an irradiation field limiter 14. The radiation source 12 includes a radiation tube (not illustrated) that generates the radiation R, and emits the radiation R generated by the radiation tube. The irradiation field limiter 14 is a so-called collimator that limits an irradiation field F of the radiation R generated by the radiation tube.

Figure 2:
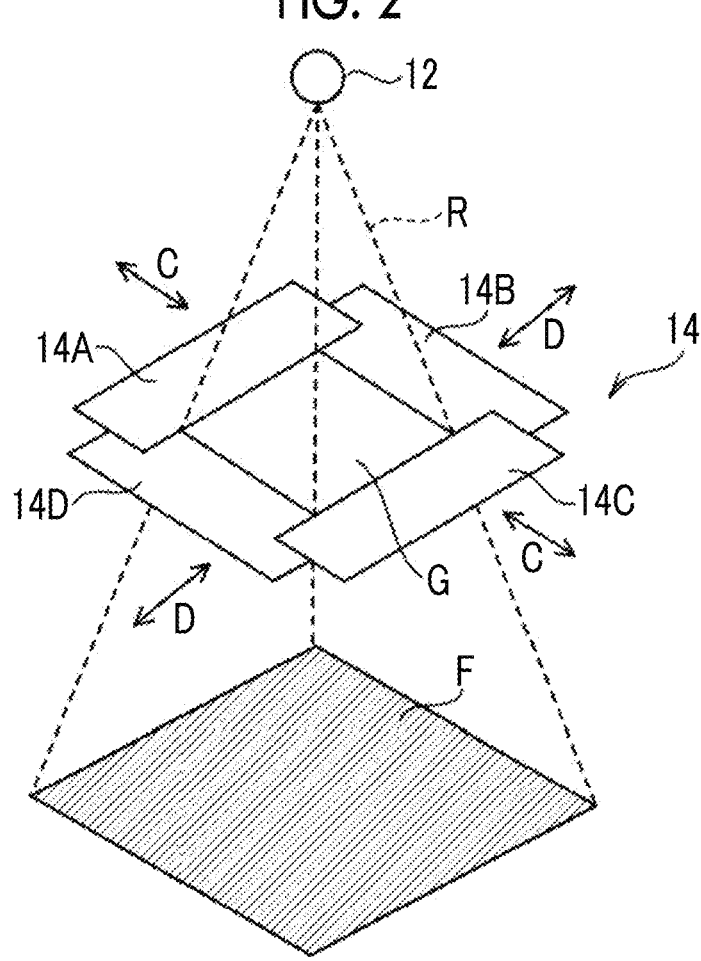
FIG. 2 is a perspective view of an irradiation field limiter seen from a front surface side on which radiation is incident.

For example, as illustrated in FIG. 2, the irradiation field limiter 14 comprises four cut-out plates 14A to 14D. The cut-out plates 14A to 14D are plate-shaped members having a rectangular shape in a plan view, in which a material such as lead or tungsten that cuts the radiation R is used. The cut-out plates 14A to 14D are disposed on respective sides of a rectangle and are configured such that an opening part G of the rectangle through which the radiation R is transmitted is formed at a center. The irradiation field limiter 14 changes a size of the opening part G by changing a position of each of the cut-out plates 14A to 14D. Accordingly, the irradiation field limiter 14 changes a range of the irradiation field F of the radiation R.

Two cut-out plates 14A and 14C move in a direction of arrow C. In addition, two cut-out plates 14B and 14D move in a direction of arrow D orthogonal to the direction of arrow C. The direction of arrow C is, for example, a direction along a set of opposite sides of a detection surface 17 of a radiation detector 38 having a rectangular shape, described later.

As illustrated in FIG. 1, the holding part 24 is provided at the other end of the arm part 22. The holding part 24 holds an accommodation part 16. The accommodation part 16 accommodates the radiation detector 38 that generates image data indicating a radiation image by detecting the radiation R. The C arm 20 of the present embodiment is configured to change an angle of the radiation detector 38 with respect to a Z axis direction illustrated in FIG. 1 (in the example in FIG. 1, a vertical direction).

Figure 3:
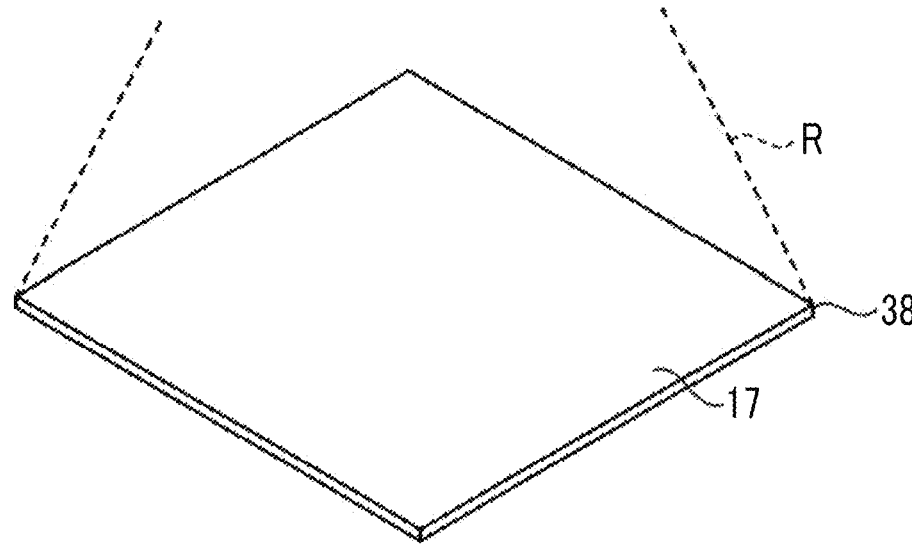
FIG. 3 is a perspective view of a radiation detector seen from the front surface side on which the radiation is incident.

The radiation detector 38 detects the radiation R that has passed through a subject. Specifically, as illustrated in FIG. 3, the radiation detector 38 detects the radiation R that has entered the accommodation part 16 and that has reached the detection surface 17 of the radiation detector 38, generates the radiation image based on the detected radiation R, and outputs the image data indicating the generated radiation image. In the present embodiment, the detection surface 17 has a rectangular shape. Hereinafter, the series of operations of generating the radiation image via the radiation detector 38 by performing irradiation with the radiation R from the radiation source 12 may be referred to as "capturing". A type of the radiation detector 38 is not particularly limited and may be, for example, a radiation detector of an indirect conversion type that converts the radiation R into light and that converts the converted light into charges or a radiation detector of a direct conversion type that directly converts the radiation R into charges. In addition, the radiation detector 38 can capture at least one of a static image or a video image.

In addition, a maximum region in which the radiation R can be detected (hereinafter, referred to as a "maximum detection region") is determined in the radiation detector 38. The maximum detection region is also a maximum region in which a valid image can be generated by the radiation detector 38 and thus, is also referred to as a maximum valid image region. For example, in a case where the radiation detector 38 is the radiation detector of the indirect conversion type, the maximum detection region corresponds to the entire region in which a sensor unit that generates and accumulates charges corresponding to light converted by a conversion layer which converts radiation into light, and a plurality of pixels including thin film transistors that convert the charges accumulated in the sensor unit into an electric signal and outputs the electric signal are disposed.

As illustrated in FIG. 1, the detection surface 17 on which the radiation R of the irradiation from the radiation emitting unit 10 is detected in the accommodation part 16 is provided to face the radiation emitting unit 10. In the radiography apparatus 1 according to the present embodiment, a so-called source image distance (SID) that is a distance between the detection surface 17 and the radiation source 12 of the radiation emitting unit 10 is a fixed value.

The C arm 20 is held to be movable in a direction of arrow A illustrated in FIG. 1 by a C arm holding part 26. In addition, the C arm holding part 26 includes a shaft part 27, and the shaft part 27 connects the C arm 20 to a bearing 28. The C arm 20 can rotate about the shaft part 27 as a rotation axis. In addition, the radiography apparatus 1 comprises a body part 18 in which a plurality of wheels 19 are provided in its bottom part. A support shaft 29 that extends and retracts in the Z axis direction in FIG. 1 is provided on an upper side of a housing of the body part 18 in FIG. 1. The bearing 28 is held to be movable in a direction of arrow B above the support shaft 29.

In addition, a display 36 and an operating part 37 are provided above the body part 18. The display 36 and the operating part 37 function as a user interface. The display 36 presents information related to the captured radiation image and capturing of the radiation image to an operator such as a technician and a doctor who capture the radiation image using the radiography apparatus 1. Examples of the display 36 include a liquid crystal display. In the present embodiment, a touch panel display in which the display 36 and the operating part 37 are integrated is applied. In addition, the operating part 37 is operated by the operator in providing an instruction related to capturing of the radiation image. Examples of the operating part 37 include various switches, a touch panel, a touch pen, and a mouse. In addition, a plurality of the operating parts 37 may be provided. For example, a touch panel and a foot switch operated by the operator using a foot may be provided as the operating parts 37.

In addition, a control device 30 that controls the irradiation field of the radiation R with which the radiation detector 38 is irradiated is accommodated inside the body part 18.

Figure 4:
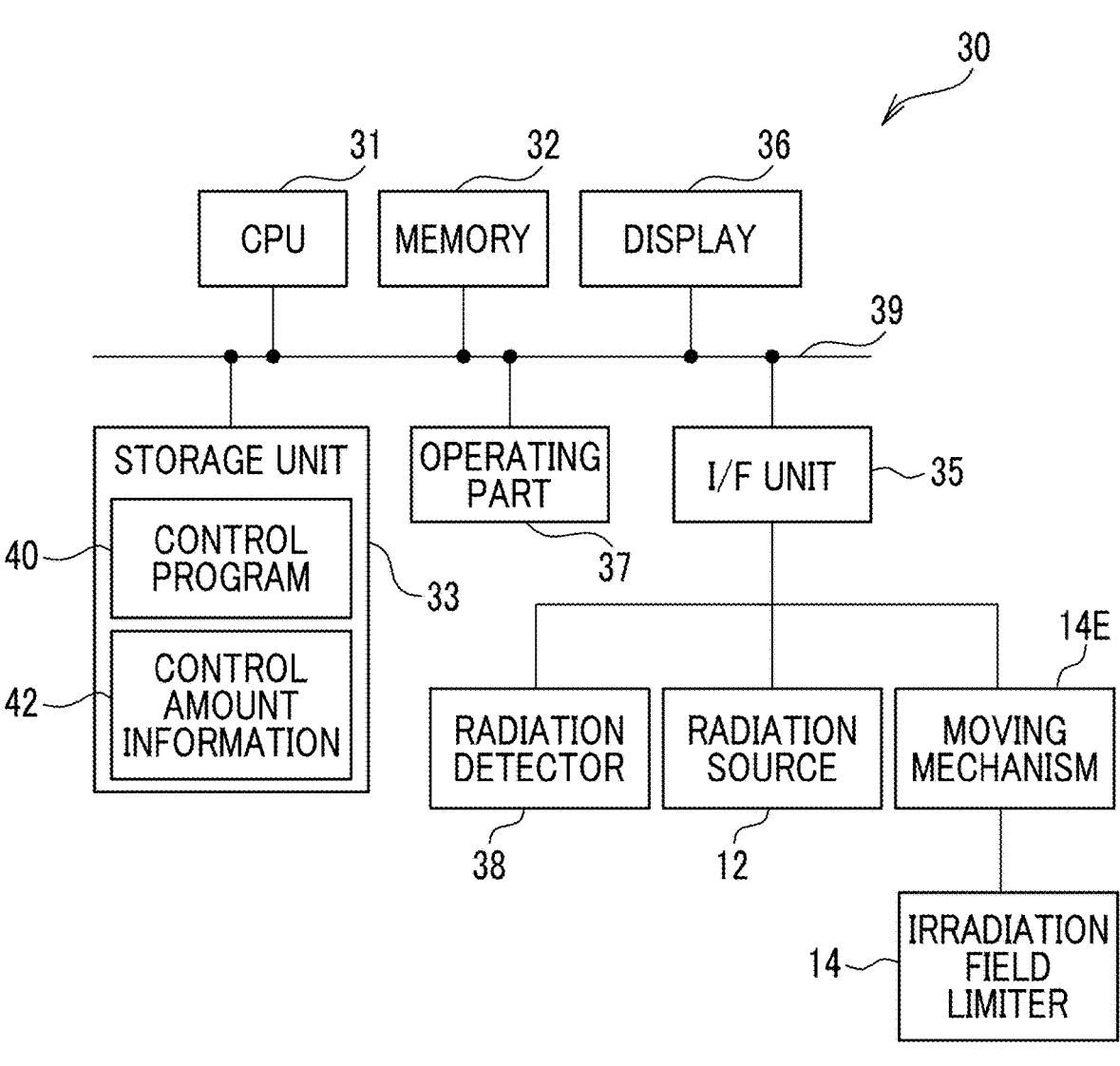
FIG. 4 is a block diagram illustrating an example of a hardware configuration of a control device.

Next, a hardware configuration of the control device 30 according to the present embodiment will be described with reference to FIG. 4. As illustrated in FIG. 4, the control device 30 includes a central processing unit (CPU) 31, a memory 32 as a temporary storage region, a non-volatile storage unit 33, an interface (I/F) unit 35, the display 36, and the operating part 37. The CPU 31, the memory 32, the storage unit 33, the I/F unit 35, the display 36, and the operating part 37 are connected to a bus 39.

The storage unit 33 is implemented using a hard disk drive (HDD), a solid state drive (SSD), a flash memory, or the like. The storage unit 33 as a storage medium stores a control program 40. The CPU 31 reads out the control program 40 from the storage unit 33 and then loads the control program 40 into the memory 32 and executes the loaded control program 40.

In addition, the storage unit 33 stores control amount information 42 including a control amount of the irradiation field limiter 14. Details of the control amount information 42 will be described later.

The radiation source 12, a moving mechanism 14E, and the radiation detector 38 are connected to the I/F unit 35. The CPU 31 can exchange various types of information with each of the radiation source 12, the moving mechanism 14E, and the radiation detector 38 through the I/F unit 35. The moving mechanism 14E moves each of the cut-out plates 14A to 14D of the irradiation field limiter 14. The moving mechanism 14E includes, for example, four motors corresponding one-on-one to the cut-out plates 14A to 14D. The CPU 31 individually controls each of the cut-out plates 14A to 14D by individually controlling each of the four motors.

Figures 5, 6:
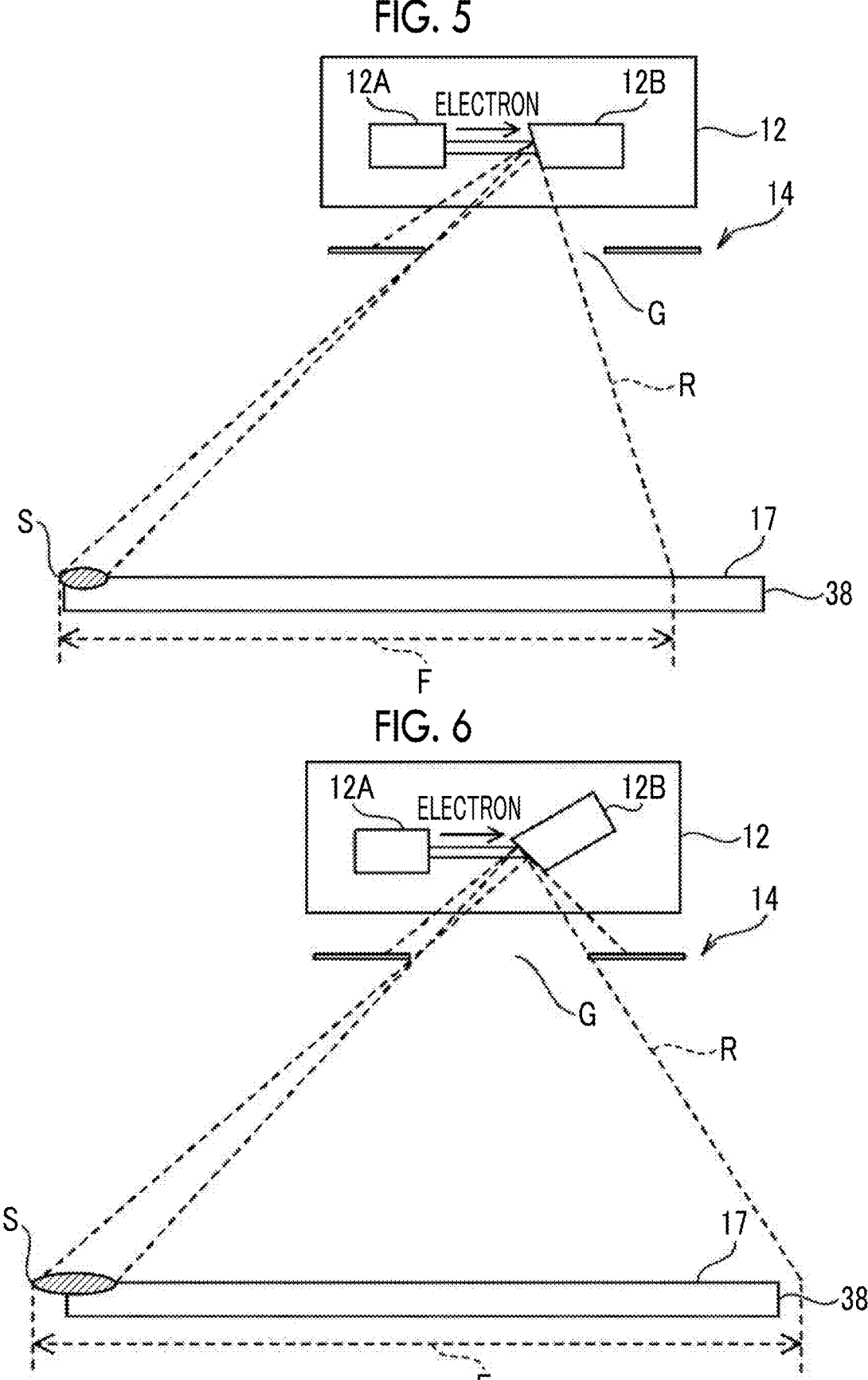
FIG. 5 is a schematic diagram for describing blurriness that occurs in a radiation image in a case where irradiation is performed with the radiation without inclining an anode of a radiation source.
FIG. 6 is a schematic diagram for describing blurriness that occurs in the radiation image in a case where the irradiation is performed with the radiation after inclining the anode of the radiation source.

For example, as illustrated in FIG. 5, in the case of capturing the radiation image by irradiating the radiation detector 38 with the radiation R from the radiation source 12, blurriness may occur in an outer edge portion of the radiation image corresponding to a region S of an end part of the irradiation field F. As a focal spot size of the radiation source 12 is increased, the blurriness is increased. In the present embodiment, the radiation source 12 includes a cathode 12A and an anode 12B, and the radiation R is generated by causing an electron beam generated from the cathode 12A to hit the anode 12B. An area of the electron beam hitting the anode 12B corresponds to the focal spot size.

In addition, for example, as illustrated in FIG. 6, the irradiation with the radiation R can also be performed after inclining the anode 12B to the detection surface 17 side with respect to a direction of a plane of the detection surface 17, in order to extend the irradiation field F without increasing the SID. In this case, the focal spot size is increased, compared to that in the case of not inclining the anode 12B. Thus, a region of the blurriness occurring in the outer edge portion of the radiation image (hereinafter, referred to as a "blurred region") is also extended.

Figure 7:
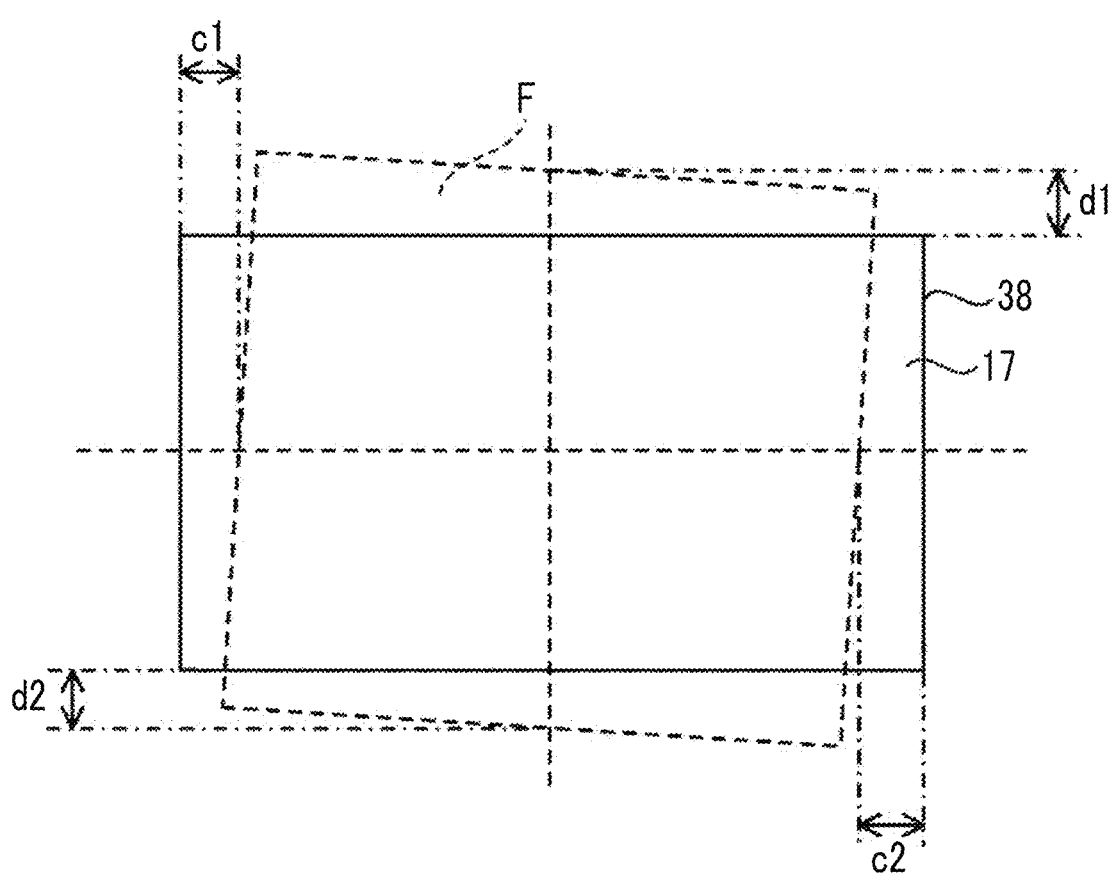
FIG. 7 is a plan view for describing an amount of deviation between an irradiation field of the radiation and a detection surface of the radiation detector.

In order to position the blurred region occurring in the outer edge portion of the radiation image as far as possible from a subject portion, it is considered to extend the irradiation field F as much as possible. However, for example, as illustrated in FIG. 7, an amount of deviation between the irradiation field F and the detection surface 17 is required to satisfy a condition determined by a standard. In FIG. 7, the irradiation field F is illustrated by a rectangle of a broken line, and the detection surface 17 is illustrated by a rectangle of a solid line. In addition, in FIG. 7, amounts of deviation between four corresponding sides of the irradiation field F and the detection surface 17 are denoted by c1, c2, d1, and d2, respectively. The condition determined by the standard is represented by, for example, Expression (1) to Expression (3) below.

$$|c1| + |c2| \leq 0.03 \times SID \tag{1}$$

$$|d1| + |d2| \leq 0.03 \times SID \tag{2}$$

$$|c1| + |c2| + |d1| + |d2| \leq 0.04 \times SID \tag{3}$$

For example, in a case where a control amount of the irradiation field limiter 14 is set as a fixed value to obtain the irradiation field F that satisfies Expression (1) to Expression (3) based on a case where an irradiation region of the radiation R required in capturing the radiation image (hereinafter, referred to as a "required irradiation region") is the maximum detection region, the blurred region occurring in the outer edge portion of the radiation image is relatively close to the subject portion even in a case where the required irradiation region is inside the maximum detection region. Therefore, the radiography apparatus 1 according to the present embodiment has a function of switching the control amount of the irradiation field limiter 14 between a case where the required irradiation region is the maximum detection region and a case where the required irradiation region is inside the maximum detection region.

In order to implement the function, the control amount information 42 includes a first control amount α and a second control amount β. For example, as illustrated in FIG.

Figure 8:
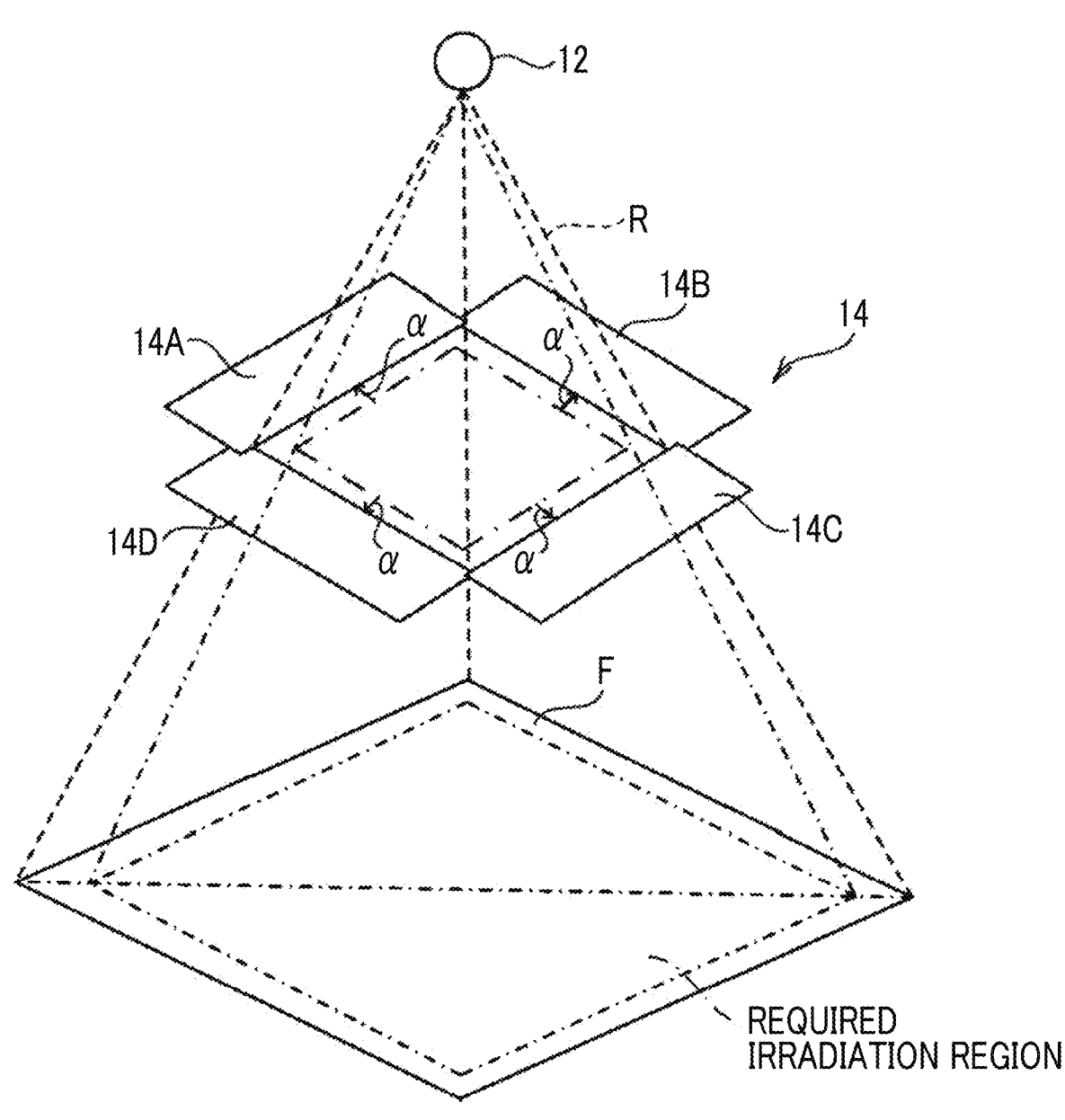
FIG. 8 is a perspective view for describing a first control amount of the irradiation field limiter.
Figure 9:
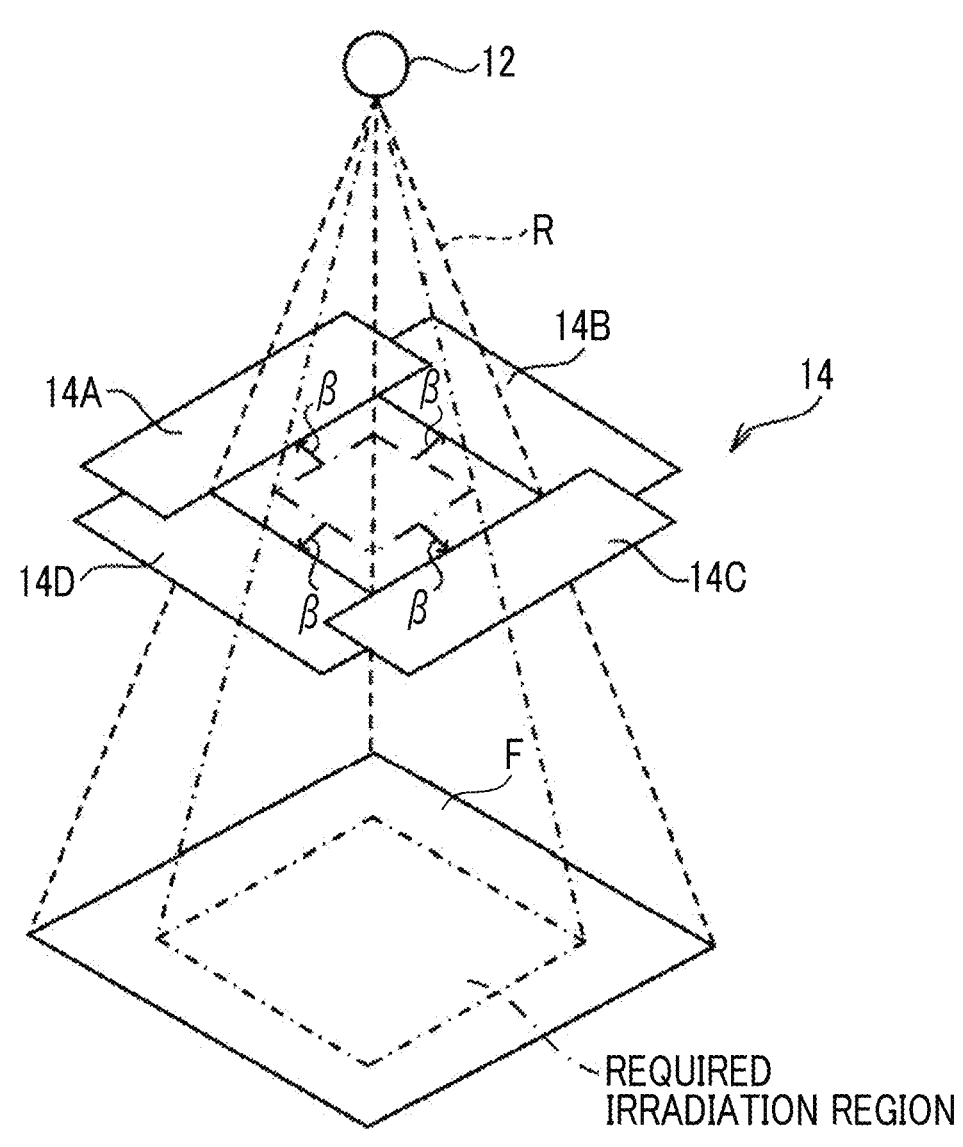
FIG. 9 is a perspective view for describing a second control amount of the irradiation field limiter.

8, the first control amount α is an amount with which the irradiation field F in a case where the required irradiation region is the maximum detection region is extended outside the required irradiation region. In FIG. 8 and FIG. 9 described later, the required irradiation region and the opening part G in a case where the irradiation field limiter 14 is controlled to match the irradiation field F to the required irradiation region are illustrated by rectangles of dot-dashed lines. In the present embodiment, an amount with which each of the cut-out plates 14A to 14D is moved outside a position to which the irradiation field limiter 14 is controlled to match the irradiation field F to the required irradiation region in a case where the required irradiation region is the maximum detection region is the first control amount α. Accordingly, the irradiation field F is extended outside the required irradiation region by an area corresponding to the first control amount α. The required irradiation region is input by the operator through the operating part 37 in accordance with, for example, a part to be imaged which is the subject and the SID. The required irradiation region may be input into an external computer and be transmitted to the control device 30 from the computer.

The first control amount α is set to a value satisfying Expression (1) to Expression (3). In the present embodiment, a value that satisfies Expression (1) to Expression (3) and that results in the maximum irradiation field F is set.

For example, as illustrated in FIG. 9, the second control amount β is an amount with which the irradiation field F in a case where the required irradiation region is inside the maximum detection region is extended outside the required irradiation region. In the present embodiment, an amount with which each of the cut-out plates 14A to 14D is moved outside from the position to which the irradiation field limiter 14 is controlled to match the irradiation field F to the required irradiation region in a case where the required irradiation region is inside the maximum detection region is the second control amount β. Accordingly, the irradiation field F is extended outside the required irradiation region by an amount corresponding to the second control amount β. The second control amount β is set to a value that satisfies Expression (1) to Expression (3) and that is greater than the first control amount α. The second control amount β is set to, for example, a value with a margin so that the above blurred region occurring in the outer edge portion does not overlap with the subject portion corresponding to the required irradiation region of the radiation image. For example, the second control amount β may be set such that an area of the irradiation field F extended in accordance with the second control amount β is less than or equal to the area of the irradiation field F extended using the first control amount α. Even in this case, Expression (1) to Expression (3) are satisfied.

Figure 10:
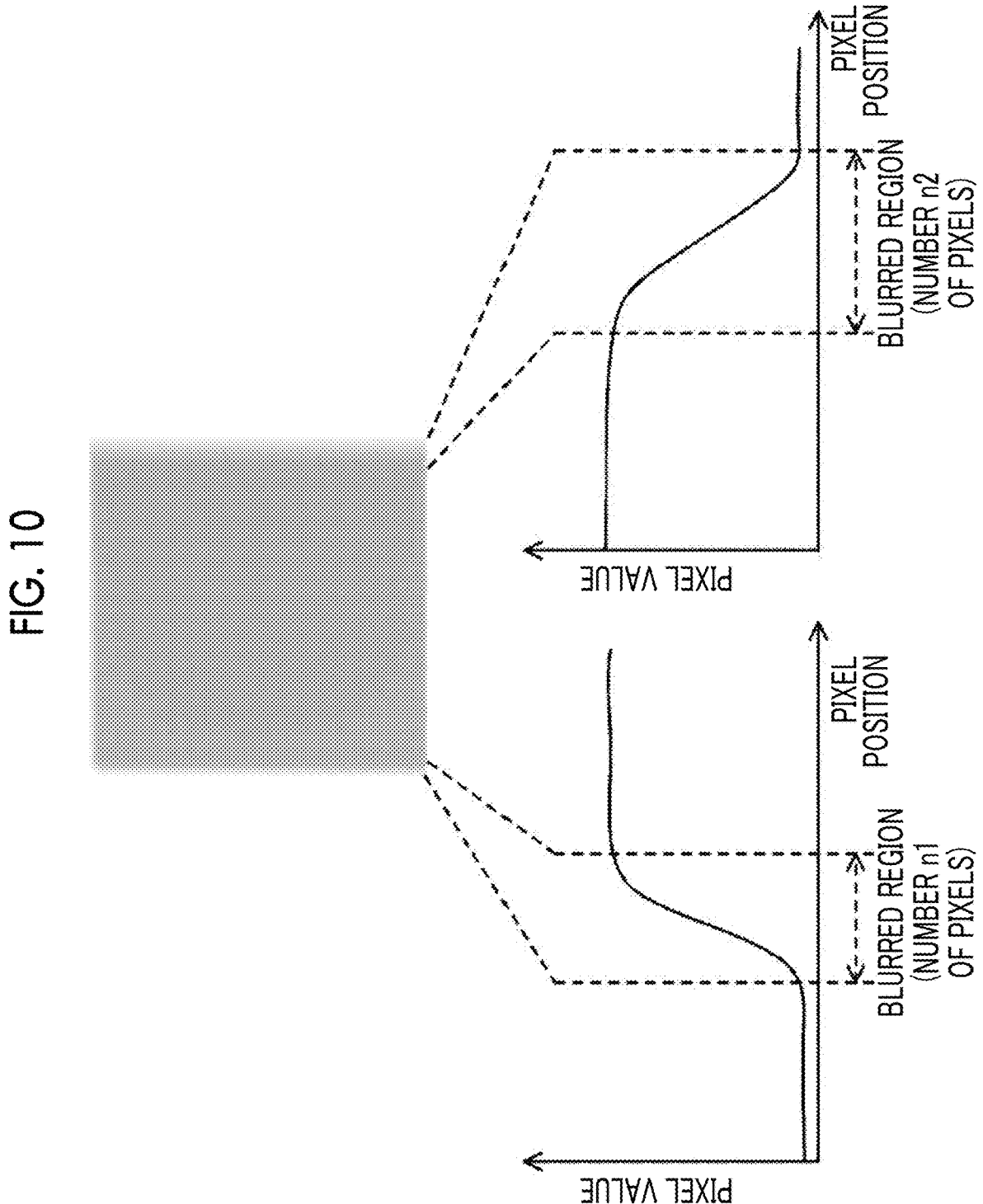
FIG. 10 is a diagram for describing the first control amount and the second control amount of the irradiation field limiter according to a modification example.

In addition, an area of the blurred region occurring in the outer edge portion of the radiation image is not necessarily a constant area on each side. For example, as illustrated in FIG. 10, the blurred region in the outer edge portion on a right side may be larger than the blurred region in the outer edge portion on a left side in FIG. 10. A gray rectangle in FIG. 10 indicates the radiation image. In addition, in two graphs in FIG. 10, a horizontal axis denotes a pixel position based on a left end of the radiation image in FIG. 10, and a vertical axis denotes an average value of pixel values in a row of the pixel position on the horizontal axis. Smoother fluctuation in the pixel values in the graphs in FIG. 10 indicates a larger blurred region.

In FIG. 10, a number n2 of pixels of a portion that corresponds to the right side of the radiation image and that has decreasing pixel values is greater than a number n1 of pixels of a portion that corresponds to the left side of the radiation image and that has increasing pixel values. That is, FIG. 10 illustrates that the blurred region in the outer edge portion on the right side is larger than the blurred region in the outer edge portion on the left side in the radiation image. Specifically, for example, in a case where the irradiation with the radiation R is performed after inclining the anode 12B of the radiation source 12 to the detection surface 17 side with respect to the direction of the plane of the detection surface 17, the blurred region in the outer edge portion on the cathode 12A side is larger than the blurred region in the outer edge portion on the anode 12B side in the radiation image. Therefore, the first control amount α and the second control amount β may be set in accordance with each side of the detection surface 17. In this case, for example, the first control amount α and the second control amount β corresponding to a side on which the blurred region is relatively large are set to values greater than the first control amount α and the second control amount β corresponding to a side on which the blurred region is relatively small.

Figure 11:
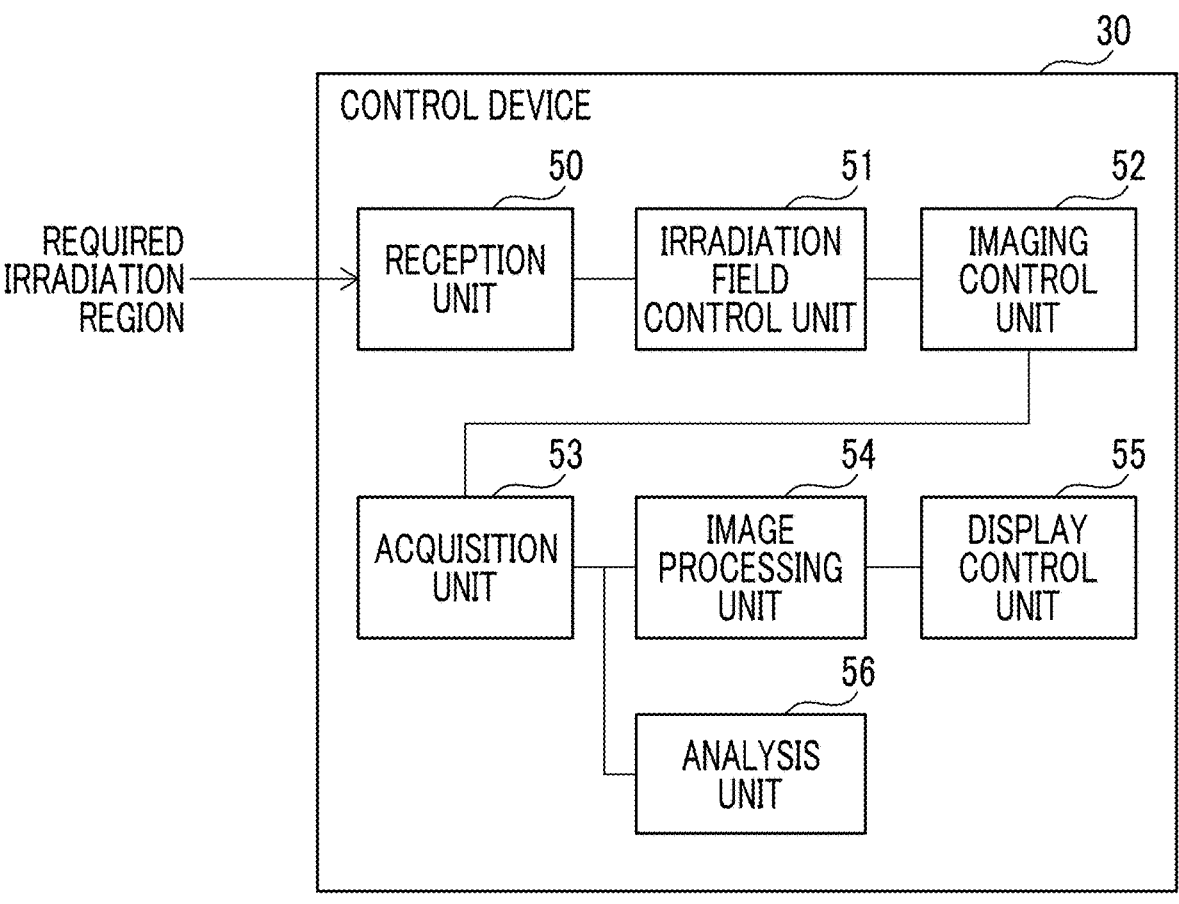
FIG. 11 is a block diagram illustrating an example of a functional configuration of the control device.

Next, a functional configuration of the control device 30 according to the present embodiment will be described with reference to FIG. 11. As illustrated in FIG. 11, the control device 30 includes a reception unit 50, an irradiation field control unit 51, an imaging control unit 52, an acquisition unit 53, an image processing unit 54, a display control unit 55, and an analysis unit 56. The CPU 31 functions as the reception unit 50, the irradiation field control unit 51, the imaging control unit 52, the acquisition unit 53, the image processing unit 54, the display control unit 55, and the analysis unit 56 by executing the control program 40.

The reception unit 50 receives an imaging condition including the required irradiation region input by the operator through the operating part 37, the tube voltage to be applied to the radiation source 12, an irradiation time of the radiation R, and the like.

The irradiation field control unit 51 acquires the control amount information 42 from the storage unit 33. In addition, in a case where the required irradiation region received by the reception unit 50 is the maximum detection region, the irradiation field control unit 51 controls the moving mechanism 14E to move the cut-out plates 14A to 14D outside from the position at which the irradiation field F matches the required irradiation region by an amount corresponding to the first control amount α included in the control amount information 42. In addition, in a case where the required irradiation region received by the reception unit 50 is inside the maximum detection region, the irradiation field control unit 51 controls the moving mechanism 14E to move the cut-out plates 14A to 14D outside from the position at which the irradiation field F matches the required irradiation region by an amount corresponding to the second control amount β included in the control amount information 42.

The imaging control unit 52 captures the radiation image by controlling the radiation source 12 in accordance with the imaging condition received by the reception unit 50.

The acquisition unit 53 acquires radiation image data indicating the radiation image captured under control of the imaging control unit 52 from the radiation detector 38.

In a case where the required irradiation region is inside the maximum detection region, the image processing unit 54 performs image processing of filling a portion outside the required irradiation region in the radiation image, which is acquired by the acquisition unit 53 and is obtained in accordance with the second control amount β, with a color set in advance. Specifically, for example, a case where the radiation image indicated by the radiation image data acquired by the acquisition unit 53 is the image illustrated in FIG. 12 will be described. In the example in FIG. 12, the outermost rectangle filled with black illustrates a display region of the radiation image in a case where the required irradiation region on the display 36 is the maximum detection region. In addition, in the example in FIG. 12, a rectangle of a dot-dashed line illustrates the radiation image indicated by the radiation image data acquired by the acquisition unit 53. In addition, in the example in FIG. 12, a dark gray portion illustrates the blurred region in the outer edge portion, and a light gray portion illustrates a portion excluding the blurred region in the outer edge portion. In addition, in the example illustrated in FIG. 12, a rectangle of a broken line illustrates a portion corresponding to the required irradiation region.

Figure 12:
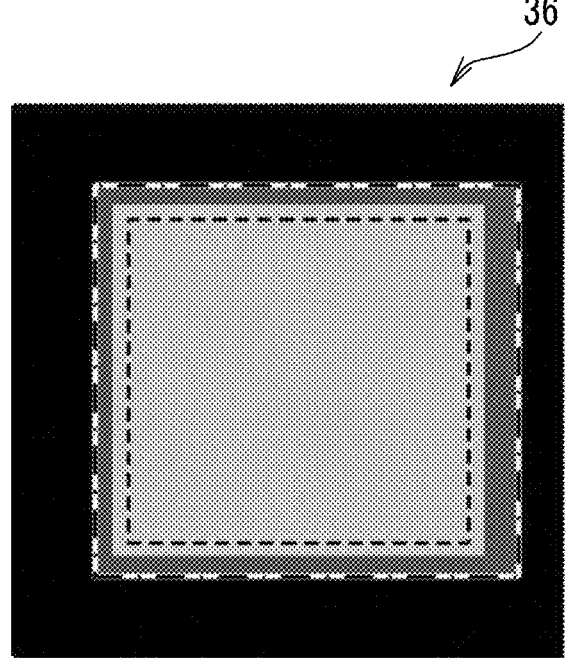
FIG. 12 is a diagram illustrating an example of a display screen in a case where image processing is not executed on an outer portion in the radiation image.
Figure 13:
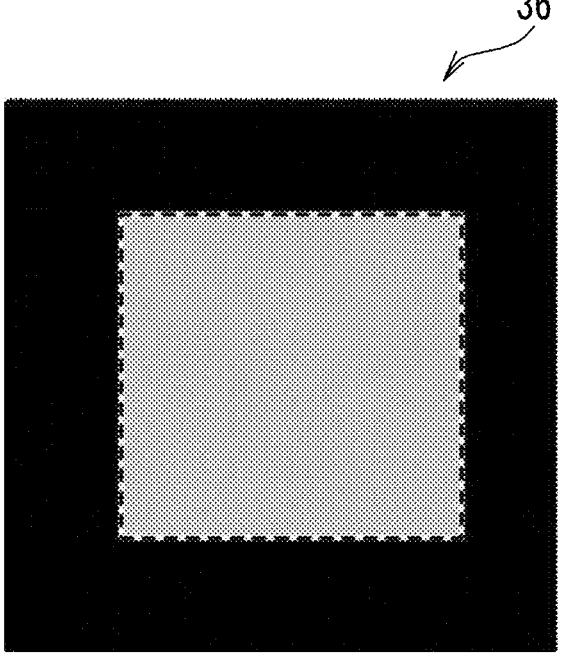
FIG. 13 is a diagram illustrating an example of the display screen in a case where the image processing is executed on the outer portion in the radiation image.

As illustrated in FIG. 13, in a case where the required irradiation region is inside the maximum detection region, the image processing unit 54 performs the image processing of filling the portion outside the required irradiation region in the radiation image with black which is a background color. As illustrated in FIG. 13, by the image processing, the dark gray portion and a portion outside the rectangle of the broken line in the light gray portion in FIG. 12 are changed to have the same color as the background color. Accordingly, the subject portion to which a diagnostician such as a doctor pays attention becomes noticeable. In a case where the required irradiation region is inside the maximum detection region, the image processing unit 54 may perform image processing of trimming to leave a portion corresponding to the required irradiation region in the radiation image obtained in accordance with the second control amount β and remove the other portion.

In a case where the required irradiation region is the maximum detection region, the display control unit 55 performs a control of displaying the radiation image indicated by the radiation image data acquired by the acquisition unit 53 on the display 36. In addition, in a case where the required irradiation region is inside the maximum detection region, the display control unit 55 performs a control of displaying the radiation image after passing through the image processing by the image processing unit 54 on the display 36.

Figure 14:
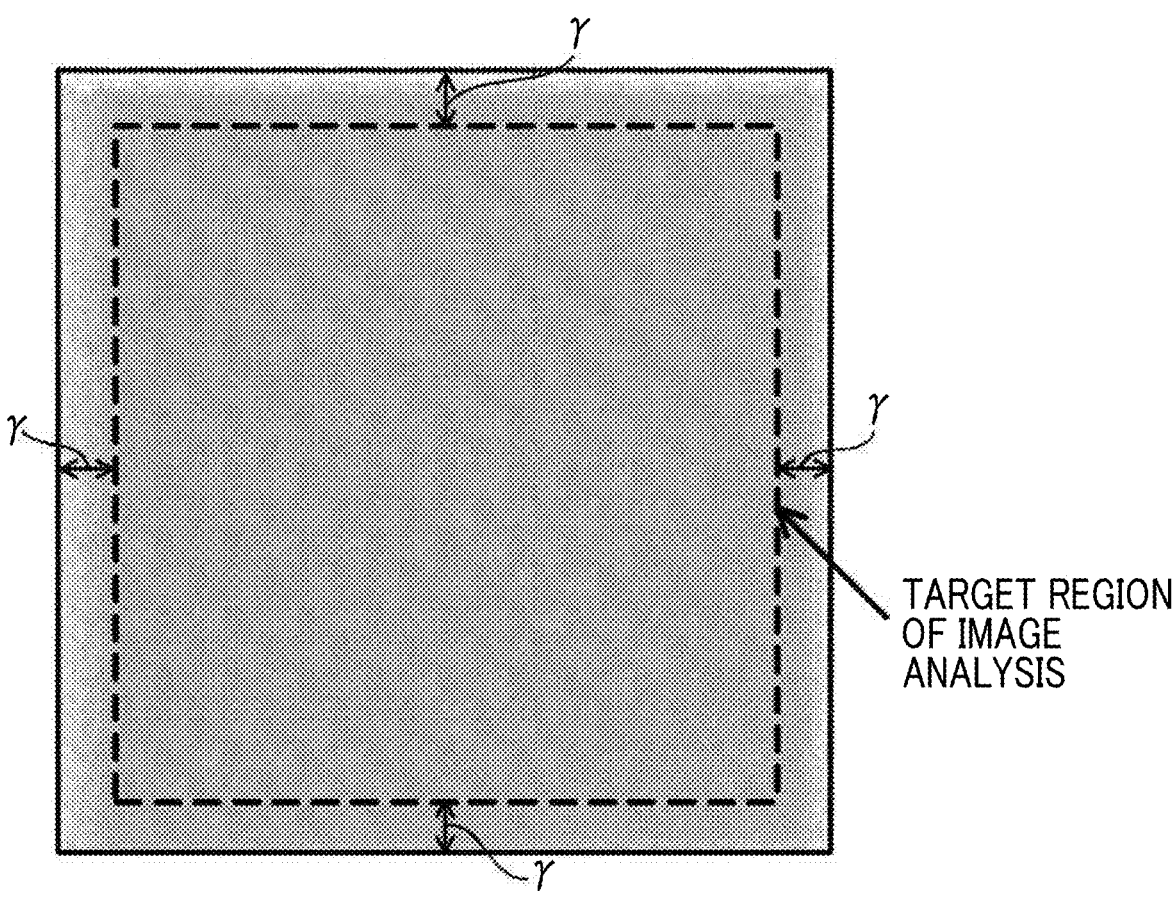
FIG. 14 is a diagram for describing a target region of image analysis.

For example, as illustrated in FIG. 14, the analysis unit 56 sets a target region of image analysis in controlling a dose of the radiation R to be inside the radiation image, which is acquired by the acquisition unit 53 and is obtained in accordance with the first control amount α or the second control amount β, by an amount corresponding to a predetermined amount γ. In the example in FIG. 14, a rectangle of a solid line illustrates the radiation image, and a rectangle of a broken line illustrates the target region of the image analysis. The predetermined amount γ is set to a value with a margin as a value with which the blurred region in the outer edge portion is not included. Accordingly, by setting the target region of the image analysis in controlling the dose of the radiation R to be inside the radiation image by the amount corresponding to the predetermined amount γ, a possibility that the blurred region is included in the target region of the image analysis is decreased. Accordingly, the dose of the radiation R can be accurately controlled.

As described above, the blurred region in the outer edge portion on the cathode 12A side may be larger than the blurred region in the outer edge portion on the anode 12B side in the radiation image. Therefore, the predetermined amount γ may be set in accordance with each side of the radiation image having a rectangular shape. In this case, for example, the predetermined amount γ corresponding to the side on which the blurred region is relatively large is set to a value greater than the predetermined amount γ corresponding to the side on which the blurred region is relatively small.

In addition, for example, the predetermined amount γ of the radiation image obtained in accordance with the first control amount α may be smaller than the predetermined amount γ of the radiation image obtained in accordance with the second control amount β. The radiation image obtained in accordance with the first control amount α means the radiation image indicated by the radiation image data acquired by the acquisition unit 53 in a case where the required irradiation region is the maximum detection region. In addition, the radiation image obtained in accordance with the second control amount β means the radiation image indicated by the radiation image data acquired by the acquisition unit 53 in a case where the required irradiation region is inside the maximum detection region.

The analysis unit 56 performs the image analysis for controlling the dose of the radiation R on a portion of a set region in the radiation image. Examples of the image analysis include processing of generating a shade histogram. For example, in a case where it is determined that the radiation image is darker than expected using the shade histogram, the radiation source 12 is controlled to increase the dose of the radiation R from the immediately previous dose in capturing the radiation image in a subsequent frame in video capturing.

Next, an action of the control device 30 according to the present embodiment will be described with reference to FIG. 15. Radiation image capturing processing illustrated in FIG. 15 is executed by executing the control program 40 via the CPU 31. The radiation image capturing processing illustrated in FIG. 15 is executed in a case where, for example, an instruction to start capturing the radiation image is input into the control device 30. In the present embodiment, it is assumed that the imaging condition including the required irradiation region, the tube voltage to be applied to the radiation source 12, the irradiation time of the radiation R, and the like is also input together with the instruction.

In step S10 in FIG. 15, the reception unit 50 receives the imaging condition including the required irradiation region input by the operator through the operating part 37, the tube voltage to be applied to the radiation source 12, the irradiation time of the radiation R, and the like. In step S12, the irradiation field control unit 51 determines whether or not the required irradiation region received in step S10 is the maximum detection region. In a case where a positive determination is made in this determination, the processing transitions to step S14.

In step S14, the irradiation field control unit 51 acquires the first control amount α included in the control amount information 42 from the storage unit 33. The irradiation field control unit 51 controls the moving mechanism 14E to move the cut-out plates 14A to 14D outside by the amount corresponding to the first control amount α from the position at which the irradiation field F matches the required irradiation region. In a case where the processing in step S16 is finished, the processing transitions to step S22.

Meanwhile, in a case where the required irradiation region received in step S10 is inside the maximum detection region, a negative determination is made in the determination in step S12, and the processing transitions to step S18. In step S18, the irradiation field control unit 51 acquires the second control amount β included in the control amount information 42 from the storage unit 33. The irradiation field control unit 51 controls the moving mechanism 14E to move the cut-out plates 14A to 14D outside by the amount corresponding to the second control amount β included in the control amount information 42 from the position at which the irradiation field F matches the required irradiation region. In a case where the processing in step S20 is finished, the processing transitions to step S22.

In step S22, the imaging control unit 52 captures the radiation image by controlling the radiation source 12 in accordance with the imaging condition received in step S10. In step S24, the acquisition unit 53 acquires the radiation image data indicating the radiation image captured under control in step S22 from the radiation detector 38.

In step S26, the image processing unit 54 determines whether or not the control amount of the cut-out plates 14A to 14D is the first control amount α, that is, whether or not the required irradiation region is the maximum detection region. In a case where a positive determination is made in this determination, the processing transitions to step S28. In step S28, the display control unit 55 performs the control of displaying the radiation image indicated by the radiation image data acquired by the acquisition unit 53 on the display 36. In a case where the processing in step S28 is finished, the processing transitions to step S34.

Meanwhile, in a case where the control amount of the cut-out plates 14A to 14D is the second control amount β, that is, in a case where the required irradiation region is inside the maximum detection region, a negative determination is made in the determination in step S26, and the processing transitions to step S30. In step S30, the image processing unit 54 performs the image processing of filling the portion outside the required irradiation region in the radiation image indicated by the radiation image data acquired in step S24 with the color set in advance. In step S32, the display control unit 55 performs the control of displaying the radiation image after passing through the image processing in step S30 on the display 36. In a case where the processing in step S32 is finished, the processing transitions to step S34.

In step S34, the analysis unit 56 sets the target region of the image analysis in controlling the dose of the radiation R to be inside the radiation image indicated by the radiation image data acquired in step S24 by the amount corresponding to the predetermined amount γ. In step S36, the analysis unit 56 performs the image analysis for controlling the dose of the radiation R on the portion of the region set in step S34 in the radiation image. As described above, a result of the image analysis in step S36 is used for controlling the dose of the radiation R in step S22 in the subsequent frame in the video capturing. In a case where the processing in step S36 is finished, the radiation image capturing processing is finished.

The processing in step S34 and step S36 may be executed before the processing in step S26 to step S32 or may be executed in parallel with the processing in step S26 to step S32.

As described above, according to the present embodiment, in a case where the required irradiation region is inside the maximum detection region, the blurred region in the outer edge portion of the radiation image is positioned outside the required irradiation region, compared to that in a case where the required irradiation region is the maximum detection region. Accordingly, a decrease in image quality of the subject portion included in the required irradiation region in the radiation image can be suppressed.

While a form of applying a mobile type radiography apparatus including a C arm as an example of a medical image capturing apparatus that captures a radiation image has been described in the embodiment, the medical image capturing apparatus is not limited to the example in the embodiment. For example, a form of the medical image capturing apparatus using a mobile cart of a mobile type including the radiation emitting unit 10 and the radiation detector 38 that is a so-called electronic cassette in combination with each other is also possible. In addition, for example, the medical image capturing apparatus may be a medical image capturing apparatus of a portable type that is carried and moved by the operator. In addition, the medical image capturing apparatus is not limited to the mobile type medical image capturing apparatus and may be a medical image capturing apparatus of a stationary type.

Figure 16:
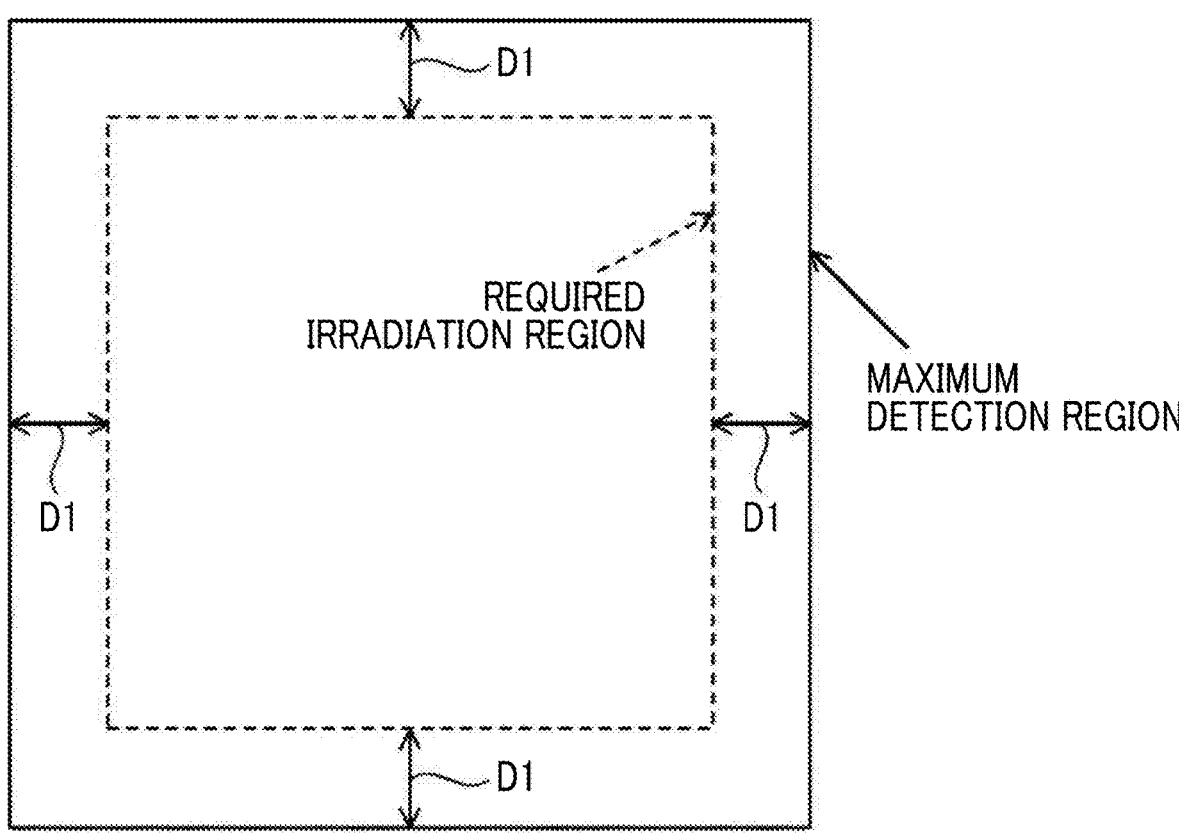
FIG. 16 is a plan view illustrating an example of a difference between a maximum detection region and a required irradiation region.

In addition, in the embodiment, the irradiation field control unit 51 may set the first control amount α and the second control amount β to the same amount in a case where a difference between the maximum detection region and the required irradiation region is less than an amount by which the irradiation field F is extended outside the required irradiation region using the first control amount α. In this case, the first control amount α and the second control amount β are the same amount in a case where the difference between the maximum detection region and the required irradiation region is relatively small. Thus, the irradiation field F extended using the second control amount β also satisfies Expression (1) to Expression (3). Here, for example, as illustrated by DI in FIG. 16, the difference between the maximum detection region and the required irradiation region means a value indicating a distance between corresponding respective sides of the maximum detection region and the required irradiation region. In the example in FIG. 16, a rectangle of a solid line illustrates the maximum detection region, and a rectangle of a broken line illustrates the required irradiation region.

In addition, in the embodiment, for example, the following various processors can be used as a hardware structure of a processing unit that executes various types of processing of the reception unit 50, the irradiation field control unit 51, the imaging control unit 52, the acquisition unit 53, the image processing unit 54, the display control unit 55, and the analysis unit 56. The various processors include, in addition to a CPU that is a general-purpose processor functioning as various processing units by executing software (program) as described above, a programmable logic device (PLD) such as a field programmable gate array (FPGA) that is a processor having a circuit configuration changeable after manufacture, a dedicated electric circuit such as an application specific integrated circuit (ASIC) that is a processor having a circuit configuration dedicatedly designed to execute specific processing, and the like.

One processing unit may be composed of one of the various processors or may be composed of a combination of two or more processors of the same type or different types (for example, a combination of a plurality of FPGAs or a combination of a CPU and an FPGA). In addition, a plurality of processing units may be composed of one processor.

As an example of the plurality of processing units composed of one processor, first, as represented by a computer such as a client and a server, a form of one processor that is composed of a combination of one or more CPUs and software and that functions as the plurality of processing units is possible. Second, as represented by a system on chip (SoC), a form of using a processor that implements functions of the entire system including the plurality of processing units in one integrated circuit (IC) chip is possible. Accordingly, various processing units are configured using one or more of the various processors as the hardware structure.

Furthermore, more specifically, an electric circuit (circuitry) in which circuit elements such as semiconductor elements are combined can be used as the hardware structure of the various processors.

In addition, while an aspect of storing (installing) the control program 40 in advance in the storage unit 33 has been described in the embodiment, the control program 40 is not limited to this aspect. The control program 40 may be provided in the form of a recording on a recording medium such as a compact disc read only memory (CD-ROM), a digital versatile disc read only memory (DVD-ROM), and a universal serial bus (USB) memory. In addition, a form of downloading the control program 40 from an external apparatus through a network is also possible.

The disclosure of JP2021-172384 filed on Oct. 21, 2021 is incorporated in the present specification by reference in its entirety. In addition, all documents, patent applications, and technical standards described in the present specification are incorporated in the present specification by reference to the same extent as in a case where individual documents, patent applications, and technical standards are specifically and individually indicated to be incorporated by reference.

What is claimed is:

1. A control device comprising:
at least one processor,
the control device controlling an irradiation field of radiation with which a radiation detector is irradiated,
wherein the processor is configured to set a first control amount to be smaller than a second control amount,
wherein the first control amount is an amount with which the irradiation field, in a case where a required irradiation region is a maximum region detectable by the radiation detector, is extended outside the required irradiation region, the required irradiation region being an irradiation region of the radiation required in capturing a radiation image, and
wherein the second control amount is an amount with which the irradiation field, in a case where the required irradiation region is inside the maximum region, is extended outside the required irradiation region.

2. The control device according to claim 1,
wherein the processor is configured to set the first control amount and the second control amount to the same amount in a case where a difference between the maximum region and the required irradiation region is less than an amount by which the irradiation field is extended outside the required irradiation region using the first control amount.

3. The control device according to claim 1,
wherein an area of the irradiation field extended in accordance with the second control amount is less than or equal to an area of the irradiation field extended using the first control amount.

4. The control device according to claim 1,
wherein a detection surface of the radiation detector for the radiation has a rectangular shape, and
the first control amount and the second control amount are set in accordance with each side of the detection surface.

5. The control device according to claim 1,
wherein the processor is configured to set a target region of image analysis in controlling a dose of the radiation to be inside a radiation image obtained in accordance with the first control amount or the second control amount by a predetermined amount.

6. The control device according to claim 5,
wherein the radiation image has a rectangular shape, and the predetermined amount is set in accordance with each side of the radiation image.

7. The control device according to claim 5,
wherein the processor is configured to set the predetermined amount of the radiation image obtained in accordance with the first control amount to be smaller than the predetermined amount of the radiation image obtained in accordance with the second control amount.

8. The control device according to claim 1,
wherein the processor is configured to:
in a case where the required irradiation region is inside the maximum region, perform image processing of filling a portion outside the required irradiation region in a radiation image obtained in accordance with the second control amount with a color set in advance; and
perform a control of displaying the radiation image after passing through the image processing on a display.

9. A control method executed by a processor of a control device including at least one processor and controlling an irradiation field of radiation with which a radiation detector is irradiated, the control method comprising:
setting a first control amount to be smaller than a second control amount,
wherein the first control amount is an amount with which the irradiation field, in a case where a required irradiation region is a maximum region detectable by the radiation detector, is extended outside the required irradiation region, the required irradiation region being an irradiation region of the radiation required in capturing a radiation image, and
wherein the second control amount is an amount with which the irradiation field, in a case where the required irradiation region is inside the maximum region, is extended outside the required irradiation region.

10. A non-transitory computer-readable storage medium storing a control program for causing a processor of a control device including at least one processor and controlling an irradiation field of radiation with which a radiation detector is irradiated, to execute:
setting a first control amount to be smaller than a second control amount,
wherein the first control amount is an amount with which the irradiation field, in a case where a required irradiation region is a maximum region detectable by the radiation detector, is extended outside the required irradiation region, the required irradiation region being an irradiation region of the radiation required in capturing a radiation image, and
wherein the second control amount is an amount with which the irradiation field, in a case where the required irradiation region is inside the maximum region, is extended outside the required irradiation region.

* * * * *